(12) United States Patent
Coulombe

(10) Patent No.: US 10,813,680 B2
(45) Date of Patent: Oct. 27, 2020

(54) CRYOBALLOON CONTACT ASSESSMENT USING CAPACITIVE OR RESISTIVE SENSORS

(71) Applicant: Medtronic CryoCath LP, Toronto (CA)

(72) Inventor: Nicolas Coulombe, Anjou (CA)

(73) Assignee: Medtronic CryoCath LP, Toronto, Ontario ( * ) Notice: Subject to any disclaimer, the term of this patent is extended or adjusted under 35 U.S.C. 154(b) by 653 days.

(21) Appl. No.: 15/470,127

(22) Filed: Mar. 27, 2017

(65) Prior Publication Data

US 2018/0271578 A1   Sep. 27, 2018

(51) Int. Cl.
*A61B 18/02* (2006.01)
*A61B 18/00* (2006.01)
*A61B 90/00* (2016.01)

(52) U.S. Cl.
CPC ...... *A61B 18/02* (2013.01); *A61B 2018/0022* (2013.01); *A61B 2018/00255* (2013.01); *A61B 2018/00375* (2013.01); *A61B 2018/00875* (2013.01); *A61B 2018/0212* (2013.01); *A61B 2090/065* (2016.02)

(58) Field of Classification Search
CPC .......... A61B 18/02; A61B 2018/00214; A61B 2018/0022; A61B 2018/0025; A61B 2018/00255; A61B 2018/00375; A61B 2018/00875; A61B 2018/0212; A61B 2090/065
See application file for complete search history.

(56) References Cited

U.S. PATENT DOCUMENTS 5,980,485 A * 11/1999 Grantz ................. A61M 25/10
                                                                    604/96.01
9,545,216 B2   1/2017 D'Angelo et al.
(Continued)

OTHER PUBLICATIONS

International Search Report and Written Opinion dated May 8, 2018, for corresponding International Application No: PCT/CA2018/050214; International Filing Date: Feb. 26, 2018 consisting of 10-pages.
(Continued)

*Primary Examiner* — Michael F Peffley
*Assistant Examiner* — Samantha M Good
(74) *Attorney, Agent, or Firm* — Christopher & Weisberg, P.A.

(57) ABSTRACT

Devices, systems, and methods for assessing contact between a treatment element and an area of target tissue using resistive-type and/or capacitive-type contact sensing elements. In one embodiment, a medical system for determining tissue contact includes an elongate body including a distal portion and a proximal portion and a treatment element coupled to the elongate body distal portion. The treatment element may have a first expandable element, a second expandable element, the first expandable element being within the second expandable element, and at least one contact sensing element between the first and second expandable elements. In one example, the device may include a plurality of contact sensing elements arranged in a matrix or in a plurality of linear configurations. In another example, the device may include a layer of conductive microparticles or a contact-sensing film.

10 Claims, 9 Drawing Sheets

(56) References Cited

U.S. PATENT DOCUMENTS

| | | | |
|---|---|---|---|
| 2003/0176816 A1* | 9/2003 | Maguire | A61B 18/00 601/2 |
| 2004/0147852 A1 | 7/2004 | Brister et al. | |
| 2006/0106375 A1 | 5/2006 | Werneth et al. | |
| 2011/0184398 A1* | 7/2011 | Desrochers | A61M 25/0069 606/21 |
| 2014/0272870 A1* | 9/2014 | Eichhorn | G09B 23/28 434/267 |
| 2015/0064675 A1* | 3/2015 | Eichhorn | A61B 34/76 434/262 |
| 2015/0164401 A1* | 6/2015 | Toth | A61B 5/04882 600/301 |
| 2015/0196740 A1* | 7/2015 | Mallin | A61B 18/02 606/21 |
| 2015/0265329 A1* | 9/2015 | Lalonde | A61B 18/02 606/21 |
| 2016/0287912 A1* | 10/2016 | Warnking | A61B 8/12 |

OTHER PUBLICATIONS

Lee et al., A transparent bending-insensitive pressure sensor, Nature Nanotechnology, vol. 11, May 2016, pp. 472-479, published online: Jan. 25, 2016 (Jan. 1, 2016), DOI: 10.1038/NNANO.2015.324.

Klinker et al., "Balloon catheters with integrated stretchable electronics for electrical stimulation, ablation and blood low monitoring", Extreme Mechanics Letters, vol. 3 (2015), pp. 45-54, Available Online Feb. 24, 2015 (Feb. 24, 2015), DOI: 10.1016/J.EML. 2015.02.005.

Lee et al., "Catheter-Based Systems With Integrated Stretchable Sensors and Conductors in Cardiac Electrophysiology", Proceedings of the IEEE, vol. 103, No. 4, Apr. 2015 (Apr. 2015), DOI: 10.1109/JPROC.2015.2401596.

Kim et al., "Electronic sensor and actuator webs for large-area complex geometry cardiac mapping and therapy", Proc Natl Acad Sci U S A. Dec. 4, 2012; 109(49): 19910-19915, Published online Nov. 12, 2012 (Dec. 11, 2012), DOI: 10.1073/pnas.1205923109.

\* cited by examiner

CRYOBALLOON CONTACT ASSESSMENT USING CAPACITIVE OR RESISTIVE SENSORS

CROSS-REFERENCE TO RELATED APPLICATION n/a

STATEMENT REGARDING FEDERALLY SPONSORED RESEARCH OR DEVELOPMENT n/a

TECHNICAL FIELD

The present invention relates to a method and system for determining contact between a treatment element and tissue based on signals from one or more contact sensing elements located within the treatment element. The one or more contact sensing elements may be resistive-type and/or capacitive-type contact sensors.

BACKGROUND

Cardiac arrhythmia, a group of disorders in which the heart's normal rhythm is disrupted, affects millions of people. Certain types of cardiac arrhythmias, including ventricular tachycardia and atrial fibrillation, may be treated by ablation (for example, radiofrequency (RF) ablation, cryoablation, microwave ablation, and the like), either endocardially or epicardially.

The effectiveness of an ablation procedure may largely depend on the quality of contact between the treatment element of the medical device and the cardiac tissue. Procedures such as pulmonary vein isolation (PVI) are commonly used to treat cardiac arrhythmias such as atrial fibrillation. In such a procedure, the treatment element may be positioned at the pulmonary vein ostium in order to create a circumferential lesion surrounding the ostium. However, proper positioning of the treatment element to create a complete circumferential lesion may be challenging.

Some current methods of assessing or monitoring tissue contact may include intra cardiac echocardiography, transesophageal echography, magnetic resonance imaging, or other currently used imaging methods. For example, current methods of assessing pulmonary vein (PV) occlusion include fluoroscopic imaging of radiopaque contrast medium injected from the device into the PV. If the treatment element, such as a cryoballoon, has not completely occluded the PV ostium, some of the contrast medium may flow from the PV into the left atrium. In that case, the cryoballoon may be repositioned and more contrast medium injected into the PV. This method not only necessitates the use of an auxiliary imaging system, but it also exposes the patient to potentially large doses of contrast medium and radiation. Additionally, contrast media techniques cannot accurately determine an exact area where lack of contact occurs, cannot be used to determine if complete circumferential contact is maintained throughout the procedure (such as an ablation procedure), and does not easily provide information about the effects of micro-movements of the treatment element on the quality of contact in real time.

Other contact assessment techniques may include using impedance, temperature, or pressure measurements. However, these methods may produce inconclusive results, as such data may be difficult to accurately measure. Further, sensors for these characteristics may not be located on an entirety of, or even most of, the treatment element. Therefore using impedance, temperature, pressure, or other such characteristics may not provide useful information about a contact status of the treatment element at enough locations to give a complete indication of tissue contact. Still other techniques such as pressure monitoring through the guidewire lumen, $CO_2$ monitoring, or the like cannot be used to pinpoint the exact location of inadequate tissue contact in real time.

Additionally, using sensors on balloons of devices designed for intracardiac use may present problems. For example, it may be difficult to secure the sensor(s) to the balloon material and avoid peeling or dislodgement of the sensor(s) during manipulation. Additionally, exposing the sensor(s) to blood, which is highly conductive, may affect sensor measurements.

SUMMARY

The present invention advantageously provides devices, systems, and methods for assessing contact between a treatment element and an area of target tissue using resistive-type and/or capacitive-type contact sensing elements. In one embodiment, a medical system for determining tissue contact includes an elongate body including a distal portion and a proximal portion and a treatment element coupled to the elongate body distal portion. The treatment element may have a first expandable element, a second expandable element, the first expandable element being within the second expandable element, and at least one contact sensing element between the first and second expandable elements.

In one aspect of the embodiment, the at least one contact sensing element includes a plurality of contact sensing elements. In one aspect of the embodiment, the plurality of contact sensing elements is in electrical communication with a multiplexer. In one aspect of the embodiment, the device further comprises a shaft having a distal tip, the multiplexer being located at the shaft distal tip.

In one aspect of the embodiment, the first expandable element has an inner surface and an outer surface, the at least one contact sensing element being on an outer surface of the first expandable element.

In one aspect of the embodiment, the second expandable element has an inner surface and an outer surface, the at least one contact sensing element being on an inner surface of the second expandable element.

In one aspect of the embodiment, the treatment element further includes an interstitial space between the first and second expandable elements, the at least one contact sensing element being in the interstitial space. In one aspect of the embodiment, the plurality of sensing elements is a matrix of sensing elements.

In one aspect of the embodiment, the plurality of sensing elements is configured in a linear array. In one aspect of the embodiment, the treatment element has a distal end and a proximal end, the plurality of sensing elements being a plurality of splines, each of the plurality of splines extending at least partially between the distal end and proximal end of the treatment element.

In one aspect of the embodiment, the at least one contact sensing element is a material containing a low density of conductive microparticles.

In one aspect of the embodiment, the at least one contact sensing element is a capacitive touch film.

In one embodiment, a medical system for determining tissue contact includes: a medical device including: an elongate body including a distal portion and a proximal portion; and a treatment element coupled to the elongate body distal portion, the treatment element having: a first expandable element; a second expandable element, the first expandable element being within the second expandable element; and at least one contact sensing element between the first and second cryoballoons; and a control unit in communication with the medical device.

In one aspect of the embodiment, the control unit includes: processing circuitry in communication with the at least one contact sensing element; and a display in communication with the processing circuitry. In one aspect of the embodiment, the at least one contact sensing element is configured to transmit electrical signals to the processing circuitry, the processing circuitry being configured to identify at last one area of the treatment element that is in contact with tissue based on the electrical signals received from the at least one contact sensing element. In one aspect of the embodiment, the processing circuitry is configured to show the identified at least one area of contact on an image of at least a portion of the treatment element.

In one aspect of the embodiment, the at least one contact sensing element is a plurality of contact sensing elements arranged in a matrix.

In one aspect of the embodiment, the at least one contact sensing element is a plurality of linear contact sensing elements.

In one aspect of the embodiment, the at least one contact sensing element is a material having a plurality of microparticles having a first conductivity when uncompressed and a second conductivity when compressed, the second conductivity being greater than the first conductivity.

In one embodiment, a method for determining tissue contact includes: positioning at least a portion of a treatment element of a medical device in contact with an area of tissue, the treatment element including: a first expandable element; a second expandable element, the first expandable element being within the second expandable element, the first and second expandable elements defining an interstitial space therebetween; and at least one contact sensing element in the interstitial space; recording electrical signals with the at least one contact sensing element and transmitting the electrical signals to a control unit; identifying with the control unit at least one area of contact between the treatment element and tissue based on the electrical signals; and displaying the at least one area of contact, the display including an image of at least a portion of the treatment element.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
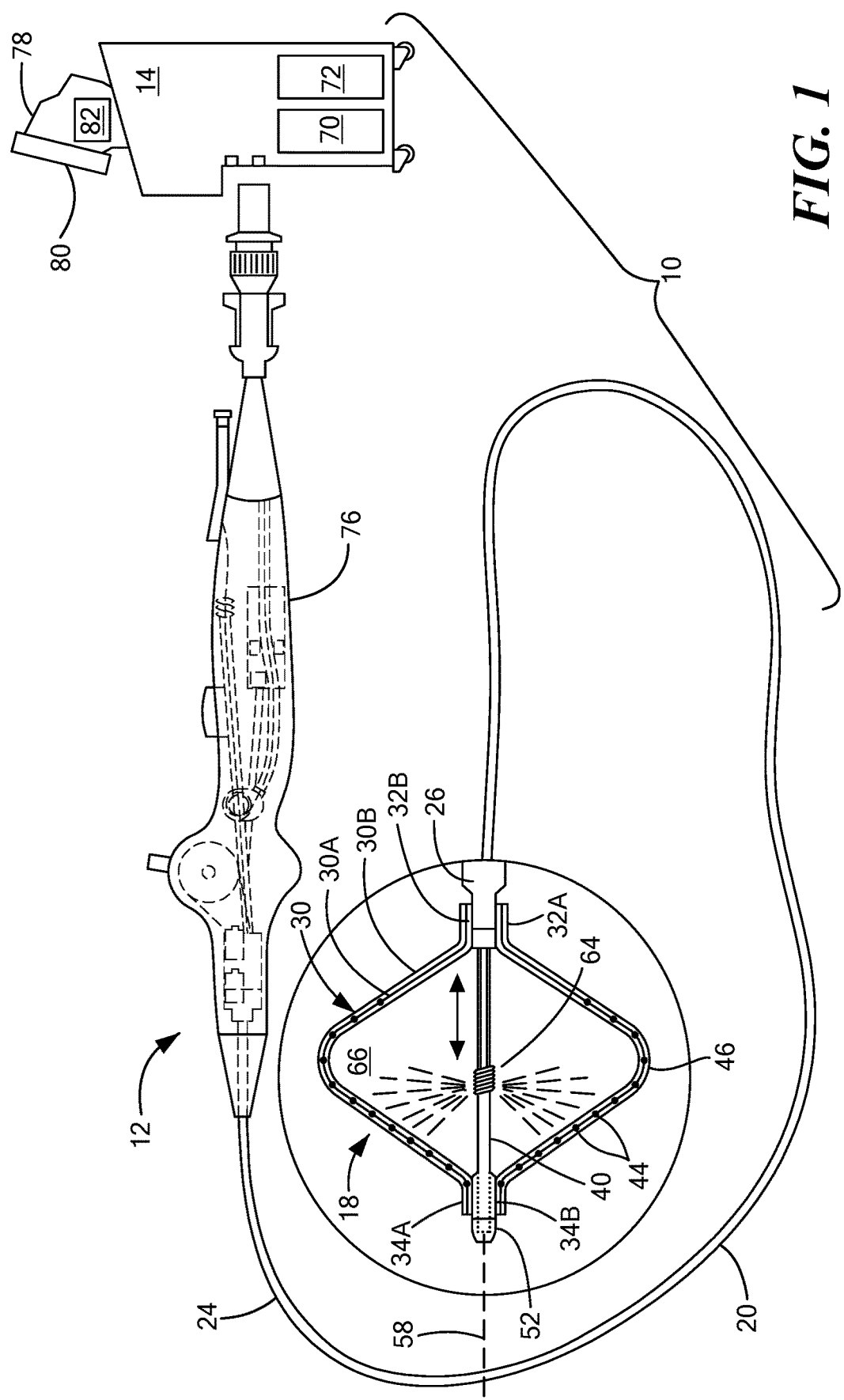
FIG. 1 shows an exemplary medical treatment system.

The devices, systems, and methods disclosed herein are for assessing contact between a treatment element and an area of target tissue using resistive-type and/or capacitive-type contact sensing elements. In one embodiment, a medical system for determining tissue contact includes an elongate body including a distal portion and a proximal portion and a treatment element coupled to the elongate body distal portion. The treatment element may have a first expandable element, a second expandable element, the first expandable element being within the second expandable element, and at least one contact sensing element between the first and second expandable elements. In one example, the device may include a plurality of contact sensing elements arranged in a matrix or in a plurality of linear configurations. In another example, the device may include a layer of conductive microparticles or a contact-sensing film.

Before describing in detail exemplary embodiments that are in accordance with the disclosure, it is noted that components have been represented where appropriate by conventional symbols in drawings, showing only those specific details that are pertinent to understanding the embodiments of the disclosure so as not to obscure the disclosure with details that will be readily apparent to those of ordinary skill in the art having the benefit of the description herein.

As used herein, relational terms, such as "first," "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

Referring now to the drawing figures in which like reference designations refer to like elements, an embodiment of a medical system is shown in FIG. 1, generally designated as "10." The device components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the system and devices disclosed herein are not necessarily exclusive of each other and may be included in a variety of different combinations or configurations without departing from the scope and spirit of the invention.

One embodiment of the system 10 may generally include a treatment device 12 in communication with a control unit 14. The treatment device 12 may include one or more diagnostic or treatment elements 18 for energetic or other therapeutic interaction between the device 12 and a treatment site. The treatment element(s) 18 may deliver, for example, cryogenic therapy, and may further be configured to deliver radiofrequency energy, or otherwise for energetic transfer with a tissue area in proximity to the treatment region(s), including cardiac tissue. In particular, the one or more treatment elements 18 may be configured to reduce the temperature of adjacent tissue in order to perform cryotreatment and/or cryoablation. For example, the treatment region(s) 18 may include one or more balloons (as shown in FIG. 1) within which a cryogenic coolant may be circulated in order to reduce the temperature of the balloon. Additionally, the treatment region(s) 18 may include other thermally and/or electrically-conductive components, such as one or more electrodes in communication with the control unit 14.

The device 12 may include an elongate body 20 passable through a patient's vasculature and/or positionable proximate to a tissue region for diagnosis or treatment, such as a catheter, sheath, or intravascular introducer. The elongate body 20 may define a proximal portion 24 and a distal portion 26, and may further include one or more lumens disposed within the elongate body 20 that provide mechanical, electrical, and/or fluid communication between the proximal portion 24 of the elongate body 20 and the distal portion 26 of the elongate body 20. Further, the one or more treatment regions 18 (such as the balloon shown in FIG. 1) may be coupled to the elongate body distal portion 26.

The one or more treatment elements 18 may include a single expandable element, as shown in the figures. However, it will be understood that the device may include more than one treatment element, including expandable and/or non-expandable treatment elements, electrodes, or other suitable energy exchange structures or components. As shown in FIG. 1, the expandable element may include a first balloon, such as a cryoballoon 30A, that has a proximal end 32A and a distal end 34A, and a second balloon, such as a cryoballoon 30B, that has a proximal end 32B and a distal end 34B. Together the first 30A and second 30B cryoballoon may be considered the expandable element of the treatment element 18 and may collectively be referred to herein as the cryoballoon 30. Also, the proximal ends 32A, 32B may be referred to herein as the proximal neck 32 of the expandable element 30 and the distal ends 34A, 34B may be referred to herein as the distal neck 34 of the expandable element 30. The expandable element proximal end 32 may be coupled to the elongate body distal portion 26 and the expandable element distal end 34 may be coupled to a shaft 40 using any suitable means. Further, the treatment element may define an interstitial space between the inner 30A and outer 30B cryoballoons. The inner 30A and outer 30B cryoballoons may be composed of the same material and may have the same degree of flexibility or compliance. Alternatively, the cryoballoons 30A, 30B may be composed of different materials that have different compliance characteristics. For example, the inner cryoballoon 30A may be at least substantially non-compliant, whereas the outer cryoballoon 30B may be at least substantially compliant.

The shaft 40 may be longitudinal movable within a lumen of the elongate body 20, such that the shaft may be advanced or retracted within the elongate body 20, and this movement of the shaft 40 may affect the shape and configuration of the cryoballoon 30. For example, the shaft 40 may be fully advanced when the cryoballoon is deflated and in a delivery (or first) configuration wherein the cryoballoon has a minimum diameter suitable, for example, for retraction of the device 12 within a sheath for delivery to and removal from the target treatment site. Conversely, when the cryoballoon is inflated and in a treatment (or second) configuration, the shaft may be advanced or retracted over a distance that affects the size and configuration of the inflated cryoballoon 30. Further, the shaft 40 may include a guidewire lumen through which a sensing device, mapping device, guidewire, or other system component may be located and extended from the distal end of the device 12.

Figure 2:
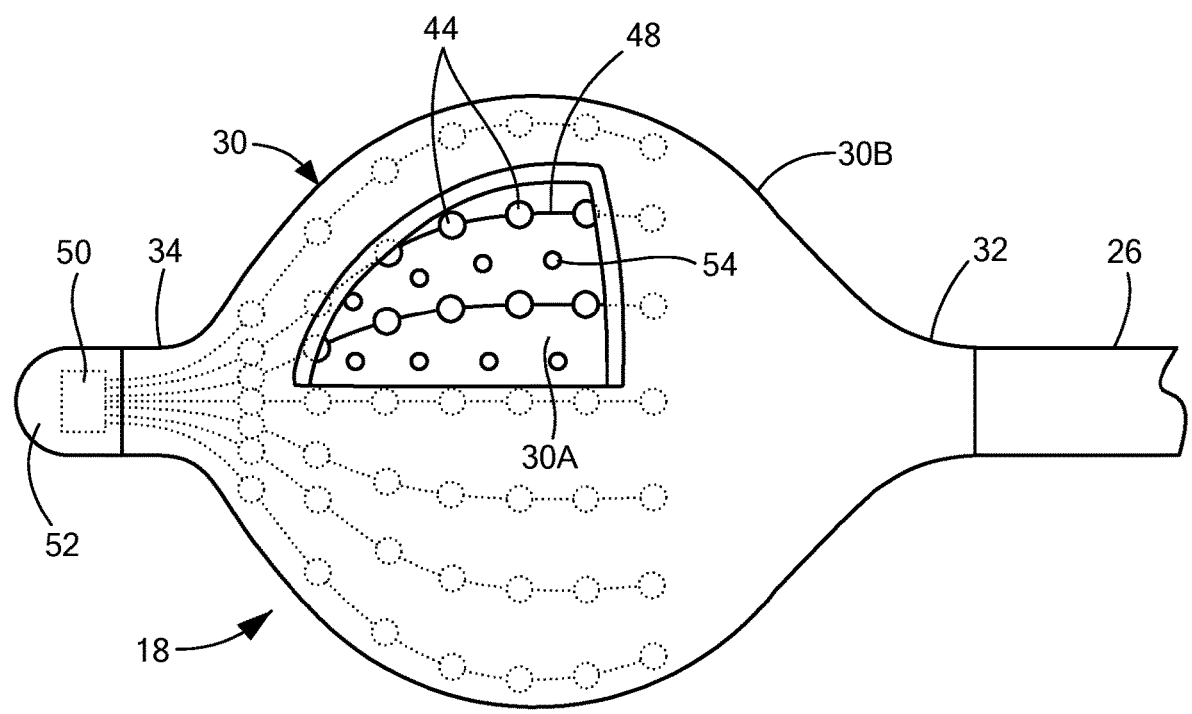
FIG. 2 shows a first close-up, partial cutaway view of a distal portion of a treatment device having a plurality of contact sensors.
Figure 3:
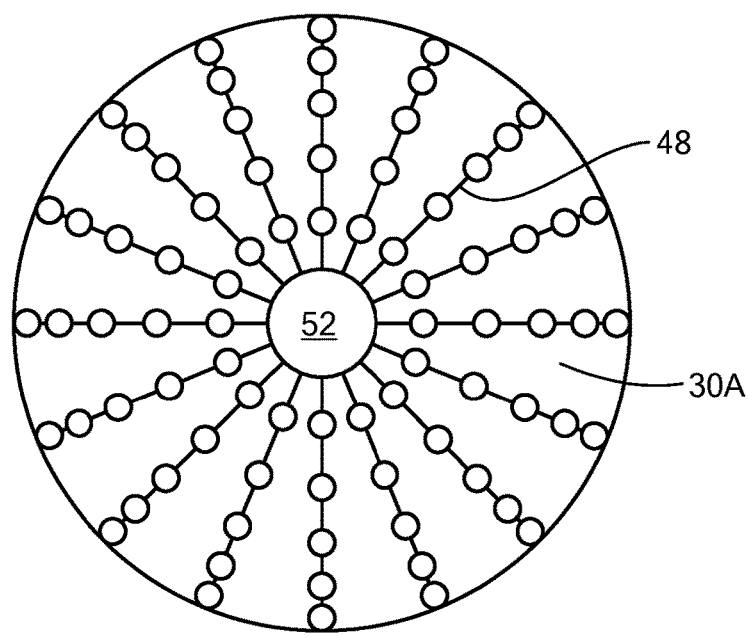
FIG. 3 shows a front view of the distal portion of the treatment device shown in FIG. 2, with an outer balloon removed.

The device 12 may further include a plurality of flexible contact sensing elements 44 disposed between the inner (or first) cryoballoon 30A and the outer (or second) cryoballoon 30B. For example, the plurality of contact sensing elements 44 may be a plurality of electrodes arranged in a matrix, mesh, or grid pattern (for example, as shown in FIGS. 2 and 3). The contact sensing elements 44 may be printed, deposited, adhered, embedded into, integrated with the material of, or otherwise at least partially present on the outer surface of the inner cryoballoon 30A or on the inner surface of the outer cryoballoon 30B. Additionally or alternatively, the contact sensing elements 44 may be unattached structures located between, and optionally held in place by, the cryoballoons 30A, 30B. In any configuration, however, the contact sensing element(s) 44 may be referred to as being between the inner 30A and outer 30B cryoballoons or within the interstitial space. As a non-limiting example, each contact sensing element 44 may be an area of one or both of the cryoballoons 30A, 30B in which the balloon material is doped with, embedded with, or having a deposited or printed layer of a biocompatible material with a predetermined conductivity selected based on the specific design of the sensor. Conductive materials may include conductive carbon including nanotubes, silver, gold, or transparent conductive oxides such as indium tin oxide, silicon indium oxide, tin oxide, or others. Materials such as inorganic conductive particles or conducting polymers may also be used for a resistive layer. Alternatively, other recently developed materials such as conductive polydimethylsiloxane, or microstructured conducting polymers made from interconnected hollow-sphere structures of polypyrrole may be used. Further, the areas in which the contact sensing elements are located may include microtextural features, such as ridges, bumps, or the like to enhance pressure measurement sensitivity.

As noted above, the flexible contact sensing elements 44 may be located between the inner 30A and outer 30B cryoballoons. This location advantageously encapsulates the contact sensing elements, effectively preventing them from dislodging them and exposing them to blood or other liquids. Additionally, a non-compliant inner cryoballoon 30A may act as the backbone of the sensor system (that is, the plurality of contact sensing elements) to impart rigidity and enable transfer of applied force on the compliant outer balloon to the sensor. This in turn may lead to a more accurate representation of the measured forces. In another embodiment, a plurality of conductive microparticles may be embedded within the polymeric balloon material, as discussed in more detail below, and arranged in such a way as to have a lower conductivity when non-compressed and higher conductivity when compressed. To effectively compress particles together with increasing force onto the sensor, a rigid backbone may also be required for adequate force transfer to the more compliant medium into which the microparticles are embedded. Using the balloon materials as the inner and outer substrates for the sensor materials may also lead to a thinner sensor design since further encapsulation of the sensor would be redundant. Thus, the treatment element profile may be kept to a minimum.

A front view of the treatment element 18 is shown in FIG. 3, with the outer balloon 30B removed for clarity. The matrix of contact sensing elements 44 may extend from a first location proximate the distal end 34 of the cryoballoon 30 (for example, a location immediately proximal to the location at which the cryoballoon distal end 34 is attached to the shaft 40, as shown in FIG. 1) to a second location that is proximal to the first location. As non-limiting examples, the matrix of contact sensing elements 44 may extend to a second location that is just distal to the cryoballoon 30 midpoint 46 when the cryoballoon 30 is inflated, a second location that is just proximal to the cryoballoon 30 midpoint 46 when the cryoballoon is inflated, or to a second location that is immediately distal to the location at which the cryoballoon proximal end 32 is attached to the elongate body distal portion 26 (which configuration may be referred to herein as the matrix extending along an entire length of the cryoballoon 30). The device 12 may include any number or configuration of contact sensing elements 44, including those numbers and configurations not shown in the figures.

Each contact sensing element 44 may be in electrical communication with a tracing or wire 48 that is in electrical communication with the control unit 14. Alternatively, more than one sensing element 44 may be in communication with a single tracing or wire. Alternatively, all of the plurality of sensing elements 44 may be in electrical communication with a multiplexer 50, which may consolidate the signals from the plurality of sensing elements 44 and transmit the combined signal to the control unit 14, which the signal may be separated into component signals by a demultiplexer in the control unit 14. As a non-limiting example, the shaft 40 may include a distal tip 52 that is either at least substantially flush with or extends distal from the cryoballoon distal end 34. The multiplexer 50 may be located on or within the shaft distal tip 52. Each contact sensing element 44 may be composed of conductive metallic materials, conductive polymeric materials, or combinations thereof. For example, the materials discussed above may be used.

In one embodiment, the treatment element 18 may function as a resistive-type touch sensor. An entirety of one of the cryoballoons 30A, 30B may include a conductive material (for example, mixed with or including a grid of tiny conductive fibers), thereby rendering the cryoballoon material a conductive layer. The contact sensing elements 44 may be included on an opposing surface of the other cryoballoon 30A, 30B. As a non-limiting example, the inner cryoballoon 30A may include a conductive material and an inner surface of the outer cryoballoon 30B may include a plurality of contact sensing elements 44. However, it will be understood that the outer cryoballoon 30B may include a conductive material and an outer surface of the inner cryoballoon 30A may include the contact sensing elements 44 (as shown in FIG. 2). The treatment element 18 may further include a plurality of spacers 54 on the outer surface of the inner cryoballoon 30A, on the inner surface of the outer cryoballoon 30B, and/or otherwise located within the interstitial space between the cryoballoons 30A, 30B (for example, as shown in FIG. 2. FIG. 3 does not show the spacers, but it will be understood that they may be included). The spacers 54 may maintain a separation (the interstitial space) between the inner 30A and outer 30B cryoballoons. When the treatment element 18 is pressed against tissue, the force may urge the cryoballoons into contact with each other in areas between the spacers 54. When the conductive contact sensing element(s) 44 of one cryoballoon come into contact with the conductive opposing cryoballoon, a current may flow between the cryoballoons 30A, 30B, and the location of the contact may be determined by the control unit 14.

In another embodiment, the treatment element 18 may function as a capacitive-type touch sensor. For example, each of the inner 30A and outer 30B cryoballoons may be composed of an insulating material, but include a conductive material, such as a grid of tiny conducive fibers, so that the cryoballoons 30A, 30B may carry a small charge. The contact sensing elements 44 may be included on the inner surface of the outer cryoballoon 30B and/or on the outer surface of the inner cryoballoon 30A. When the outer cryoballoon 30B comes into contact with tissue, the charge of the outer cryoballoon 30B in that area may change. The matrix of contact sensing elements 44 may function as sensors that measure this change and communicate the location of the change to the control unit 14.

Figure 4:
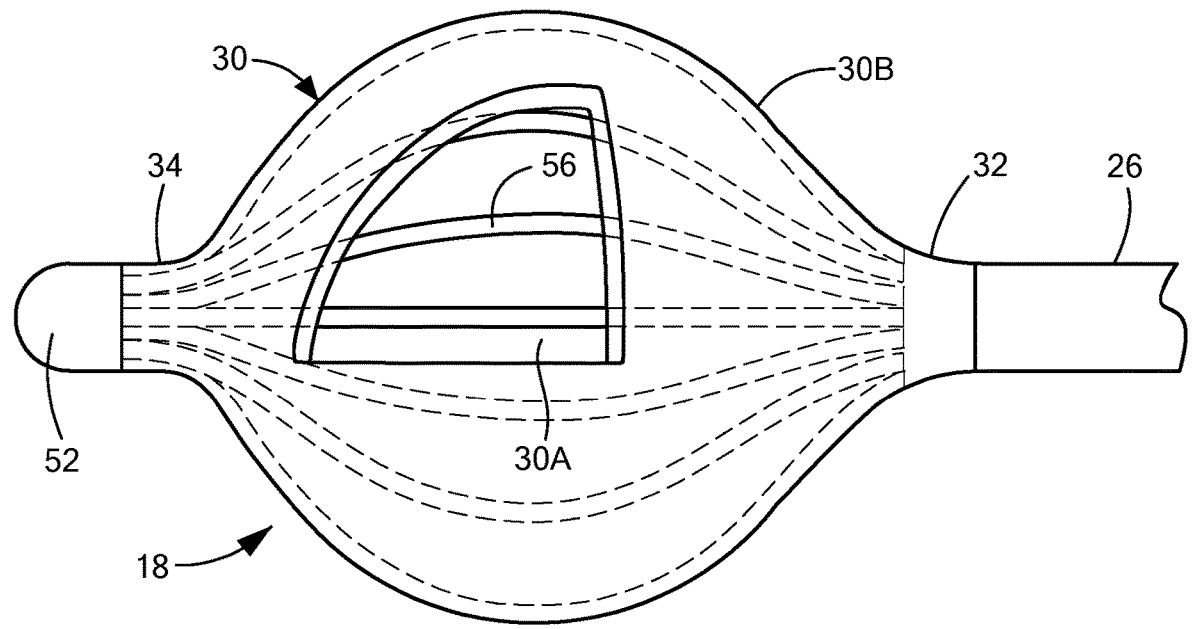
FIG. 4 shows a second close-up, partial cutaway view of a distal portion of a treatment device having a plurality of contact sensors.
Figure 5:
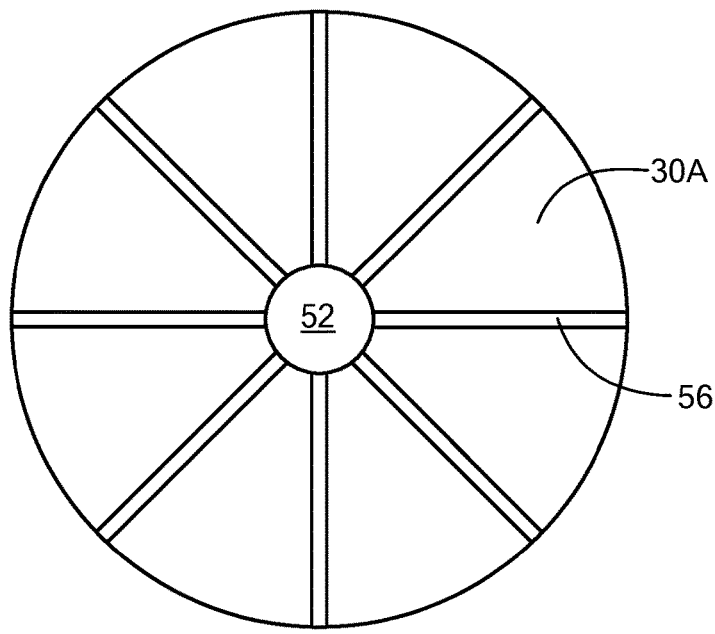
FIG. 5 shows a front view of the distal portion of the treatment device shown in FIG. 4, with an outer balloon removed.

Referring to FIGS. 4 and 5, an alternative embodiment of a treatment element 18 is shown. The features of the treatment element 18 shown in FIGS. 4 and 5 may be the same as or substantially the same as those of the treatment element shown in FIGS. 2 and 3. Further, it will be understood that the treatment element 18 may include spacers 54 if used as a resistive-type touch sensor. However, the contact sensing elements 44 may be or include a plurality of splines 56 located between the inner cryoballoon 30A and the outer cryoballoon 30B (for example, the splines may be located within the cryoballoon interstitial space). A front view of the treatment element 18 is shown in FIG. 5, with the outer balloon 30B removed for clarity. Each spline 56 may extend from the cryoballoon distal end 34 to the cryoballoon proximal end 32, and may continue to extend in a distal-to-proximal direction within the elongate body 20, toward the control unit 14. Alternatively, a proximal end of each spline 56 may be coupled to, and end at, the elongate body distal portion 26. Further, the spline distal ends may be coupled to the shaft 40 or shaft distal tip 52. The splines 56 may be symmetrically disposed around the longitudinal axis 58 (or the longitudinal axis of the elongate body, if the device does not include a shaft 40), like the segments of an orange, in a basket configuration. Each spline 56 may be in electrical communication with a tracing or wire, and optionally to a multiplexer 50. The device 12 may include any number or configuration of splines 56, including those numbers and configurations not shown in the figures. The splines may be a linear array of sensors, wires of conductive material, and/or a continuous areas of conductive material that is printed, deposited, adhered, embedded into, integrated with the material of, or otherwise at least partially present on the outer surface of the inner cryoballoon 30A, or on the inner surface of the outer cryoballoon 30B, in a linear arrangement. For simplicity, any of these configurations may be referred to herein as a spline. The splines may be composed of one or more materials such as copper, gold, silver, or any other suitable biocompatible and flexible conductive metal, polymer, or combination thereof.

Figure 6:
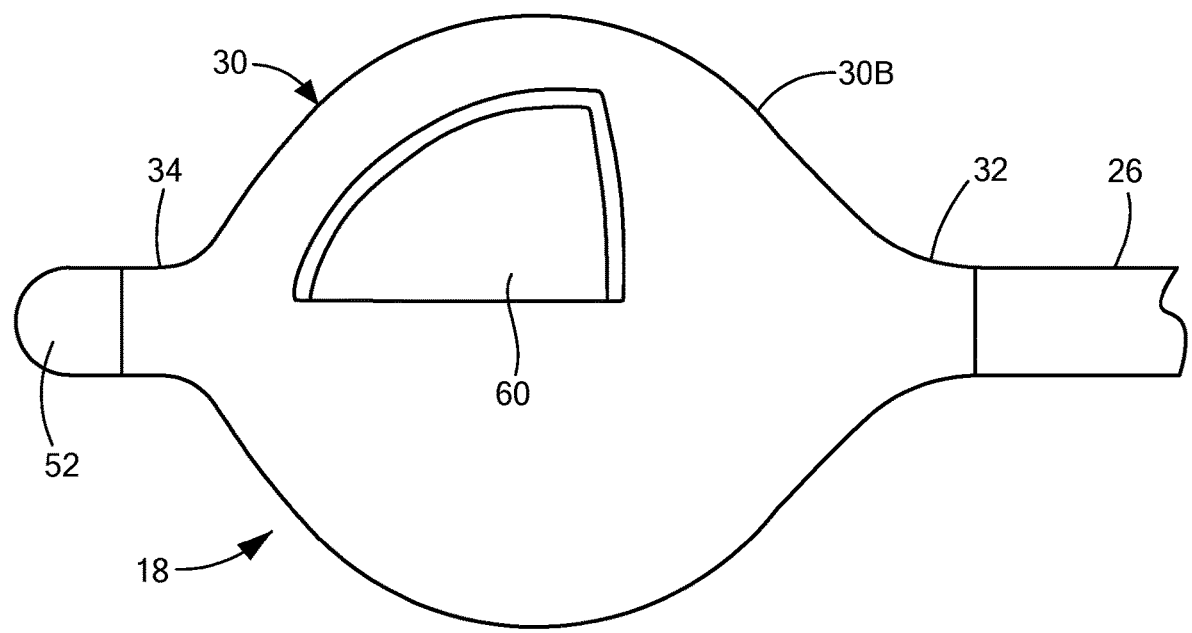
FIG. 6 shows a third close-up, partial cutaway view of a distal portion of a treatment device having a contact sensor.

Referring to FIG. 6, an alternative embodiment of the treatment element is shown, in which a layer of flexible capacitive touch film 60 is located between the inner 30A and outer 30B cryoballoons (for example, the film may be located within the cryoballoon interstitial space). Rather than including a plurality of individual contact sensing elements 44, the flexible film 60 shown in FIG. 6 may be referred to as a single contact sensing element 44. However, the flexible film 60 may be capable of registering a plurality of simultaneous touch points at any location on the film. The film 60 may be in electrical communication with the control unit 14. The film may detect contact between the cryoballoon 30 and tissue through capacitive changes wherein an electrical charge is transferred from the tissue to complete a circuit, causing a voltage drop on that point on the film 60. The outer cryoballoon 30B may be embedded or impregnated with conductive fibers that allow charge transfer from the tissue to the film 60. Alternatively, the expandable element may include only one cryoballoon 30, and the film 60 may be located on an outer surface of the cryoballoon 30 such that the film 60 directly contacts tissue when the device is in use. The film may have any suitable size or configuration. For example, the film 60 may cover less than an entirety of the outer surface of the inner balloon 30A.

Figure 7:
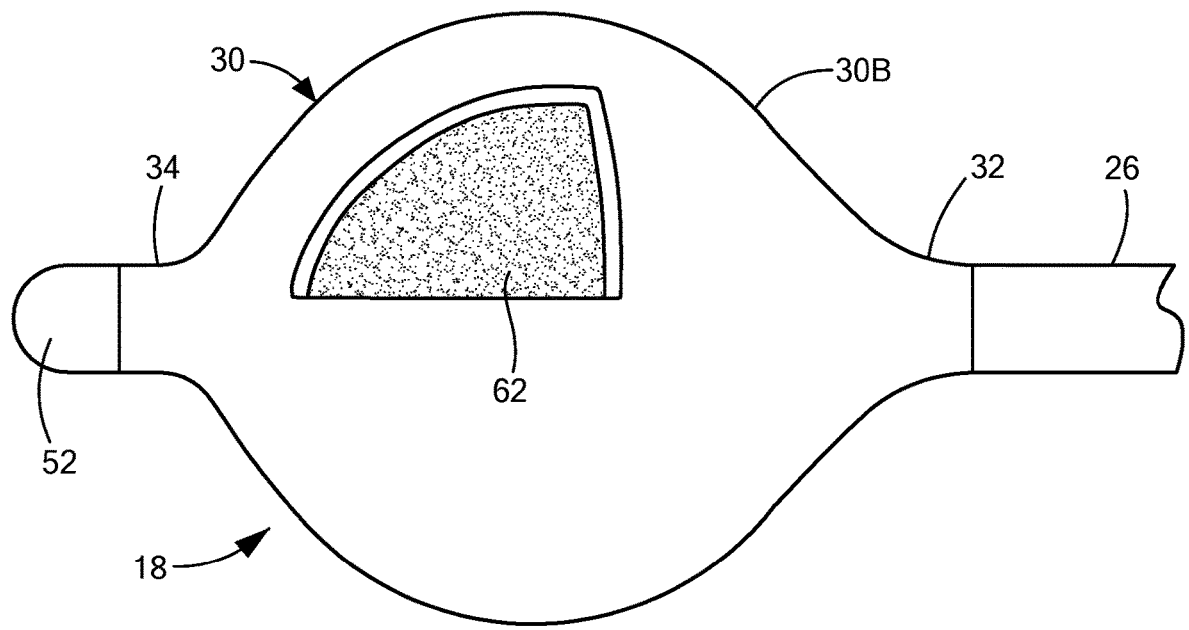
FIG. 7 shows a fourth close-up, partial cutaway view of a distal portion of a treatment device having contact sensing capabilities.

Referring to FIG. 7, an alternative embodiment of the treatment element is shown, in which the material of the inner cryoballoon 30A and/or the outer cryoballoon 30B may be doped with or may contain a low density of conductive microparticles 62 that provide contact sensing capabilities to the treatment element 18. Alternatively, a material containing the conductive microparticles 62 may be included within the interstitial space between the cryoballoons 30A, 30B. These microparticles 62 collectively may be referred to as a contact sensing element 44. This material may function as a piezoresistive sensor, transducing mechanical strain into an impedance change. For example, when the cryoballoon(s) 30 are not compressed (that is, not in contact with tissue and exerting a force against the tissue or receiving a compressive force from the tissue or other structure), the microparticles, and therefore the cryoballoon(s) 30, are weakly conductive or have a relatively high resistance. When the cryoballoon(s) are compressed, the microparticles 62 may come into contact with each other, thereby increasing their conductivity and, in turn, conducting a signal through the cryoballoon(s) 30. As a non-limiting example, the microparticles 62 may be composed of electrically conductive carbon, including carbon nanotubes, polypyrrole, polypyrrole-coated polyurethane, or other suitable materials.

Figure 8:
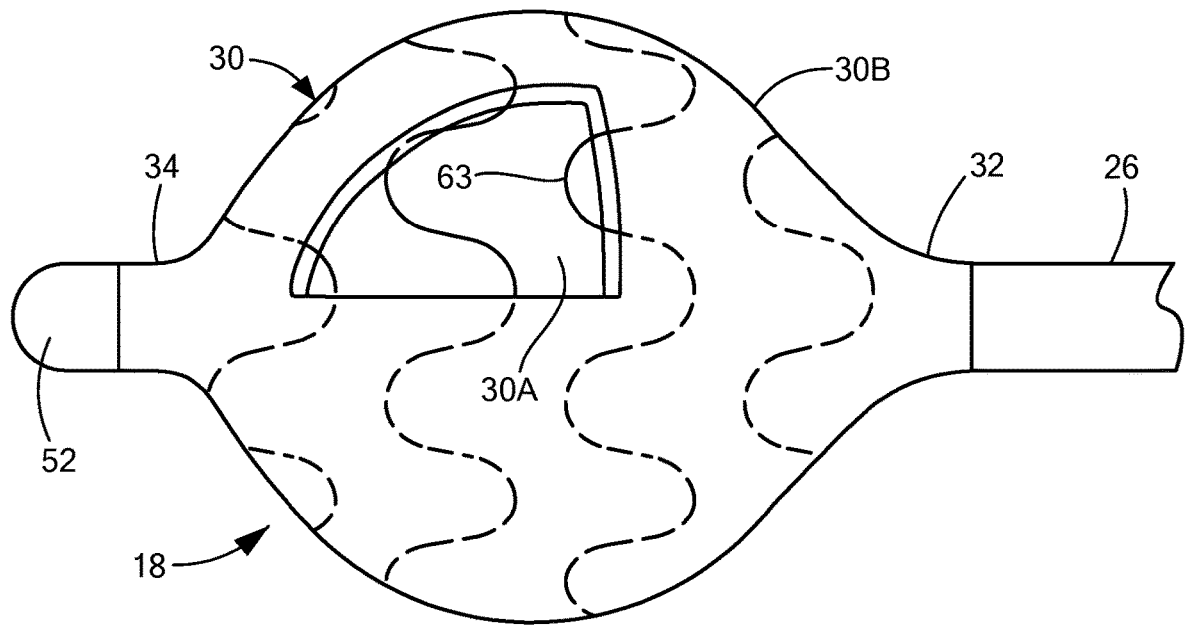
FIG. 8 shows a fifth close-up, partial cutaway view of a distal portion of a treatment device having a contact sensing element.
Figure 9:
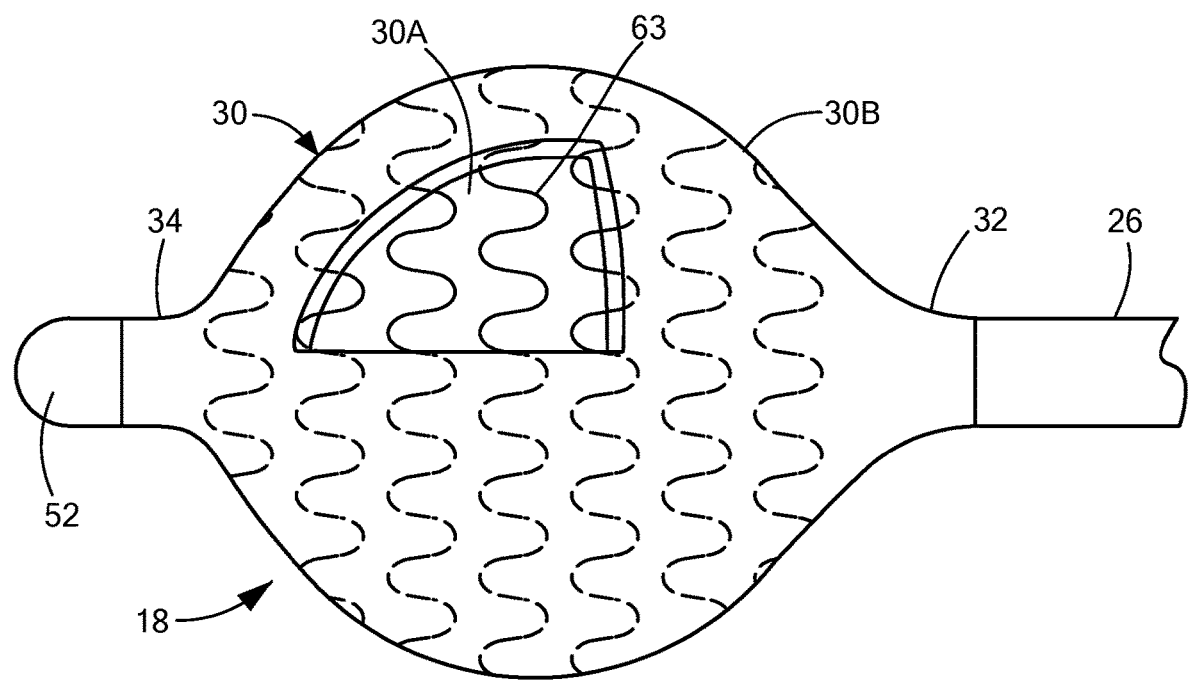
FIG. 9 shows a sixth close-up, partial cutaway view of a distal portion of a treatment device having a contact sensing element.
Figure 10:
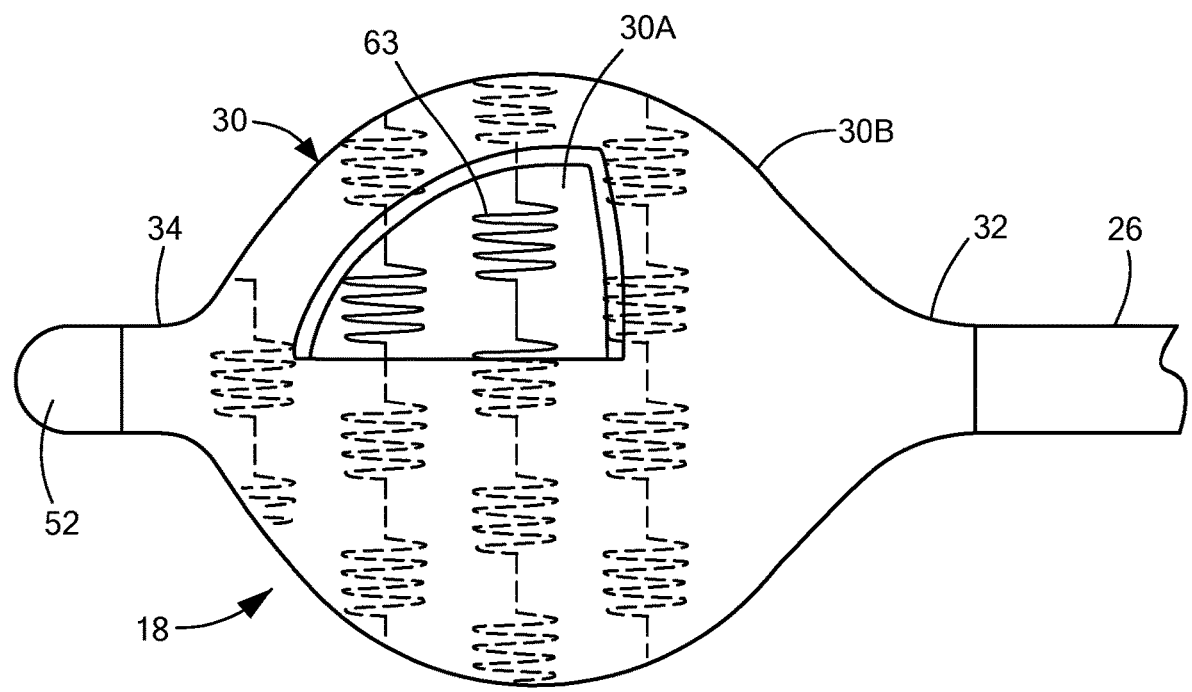
FIG. 10 shows a seventh close-up, partial cutaway view of a distal portion of a treatment device having a contact sensing element.

Referring to FIGS. 8-10, additional embodiments of a treatment element are shown. The features of the treatment element 18 shown in FIGS. 8-10 may be the same as or substantially the same as those of the treatment element shown in FIGS. 2 and 3. Further, it will be understood that the treatment element 18 may include spacers 54 if used as a resistive-type touch sensor. However, the device may include at least one filamentous contact sensing element 63 located between the inner cryoballoon 30A and the outer cryoballoon 30B (for example, the filamentous contact sensing element may be located within the cryoballoon interstitial space). If the treatment element 18 includes only one filamentous contact sensing element 63, the contact sensing element 63 may be wound around the inner cryoballoon 30A from a proximal location on the cryoballoon 30A to a distal location on the cryoballoon 30A. If the treatment element 18 includes more than one filamentous contact sensing element 63, each sensing element may be wound around the inner cryoballoon 30A from a proximal location on the cryoballoon 30A to a distal location on the cryoballoon 30A or, alternatively, each filamentous contact sensing element 63 may at least partially encircle a circumference of the inner cryoballoon 30A (that is, be arranged as bands that extend around the shaft longitudinal axis 58).

Further, each filamentous contact sensing element 63 may have a wavy or undulating pattern (for example, as shown in FIGS. 8 and 9), zigzag pattern (for example, as shown in FIG. 10), or other configuration that increases the surface area over with the filamentous contact sensing element(s) 63 is/are disposed while enabling the balloon to be stretched or deformed without damaging filaments due to material strain, as well as facilitating foldability of the balloon when deflated. Like the splines 56 described above, the filamentous contact sensing elements 63 may be a linear array of sensors, wires of conductive material, and/or a continuous areas of conductive material that is printed, deposited, adhered, embedded into, integrated with the material of, or otherwise at least partially present on the outer surface of the inner cryoballoon 30A, or on the inner surface of the outer cryoballoon 30B, or otherwise within the interstitial space. The filamentous contact sensing elements 63 may be composed of one or more materials such as copper, gold, silver, or any other suitable biocompatible and flexible conductive metal, polymer, or combination thereof.

Referring again to FIG. 1, the device may include one or more nozzles, orifices, or other fluid delivery elements 64 for delivering fluid to the interior chamber 66 of the cryoballoon 30. During operation, coolant may flow from a coolant supply 70 through a coolant delivery conduit within the cryoablation device elongate body 20 to the distal portion 26, where the coolant may then enter the interior chamber 66 of the cryoballoon 30, such as through the one or more fluid delivery elements 32, where the coolant may expand to cool the cryoballoon 30. Expanded coolant may then pass from the interior chamber 66 of the cryoballoon 30 to a coolant recovery reservoir 72 and/or scavenging system through a coolant recovery conduit.

The device 12 may further include a handle 76 coupled to the elongate body proximal portion 24, and the handle 76 may include one or more steering or deflection components for manipulating the elongate body 20, the one or more treatment elements 18, and/or additional components of the device 12. The handle 76 may also include connectors that are matable directly or indirectly to the control unit 14 to establish communication between the one or more components of the device 12 with one or more components of the control unit 14, as described herein. For example, in an exemplary system, the coolant supply 70, coolant recovery reservoir 72, and/or one or more alternative energy sources to supply the selected modality of treatment to the treatment element(s) 18 (such as, for example, a radiofrequency generator, ultrasound generator, light sources, or the like) as well as various control mechanisms for the system 10 may be housed in the control unit 14. The control unit 14 may also include one or more computers 78 having one or more displays 80 and processing circuitry and/or software modules 82. The processing circuitry 82 may be programmed or programmable to execute the automated operation and performance of the features, sequences, or procedures described herein. As a non-limiting example, the processing circuitry 82 may include a memory and a processor, the memory in communication with the processor and having instructions that, when executed by the processor, configure the processor to perform one or more system functions. For example, the processing circuitry 82 may be configured to receive electrical signals from the contact sensing element(s) 44 (including the splines 56 and/or the filamentous contact sensing element(s) 63) and identify contact locations on the cryoballoon 30 from those signals. It will be understood that one or more system components may be physically located outside of the control unit 14; however, any system components that are not part of the device 12 may be referred to herein as being located within the control unit 14 for simplicity.

The device 12 and/or control unit 14 may also include one or more sensors to monitor the operating parameters throughout the system 10, including for example, pressure, temperature, flow rates, volume, or the like in the control unit 14, and/or the device 12. For example, the device 12 may further include one or more temperature and/or pressure sensors (not shown) proximate the treatment element(s) 18 for monitoring, recording or otherwise conveying measurements of conditions within the device 12 or the ambient environment at the distal portion of the cryoablation device 12. The sensor(s) may be in communication with the control unit 14 for initiating or triggering one or more alerts or therapeutic delivery modifications during operation of the device 12.

Figure 11:
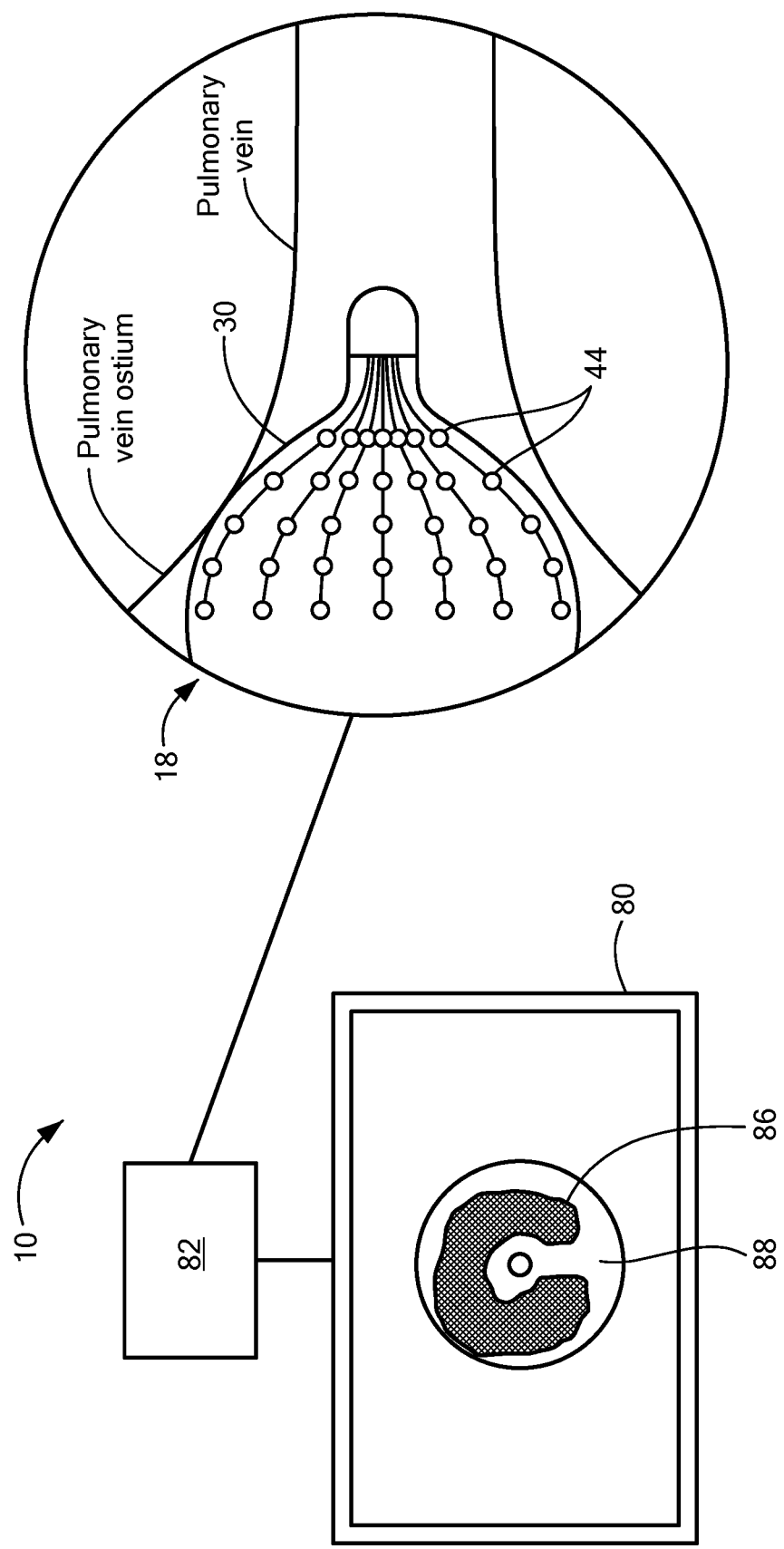
FIG. 11 shows a first simplified medical treatment system with informational display.
Figure 12:
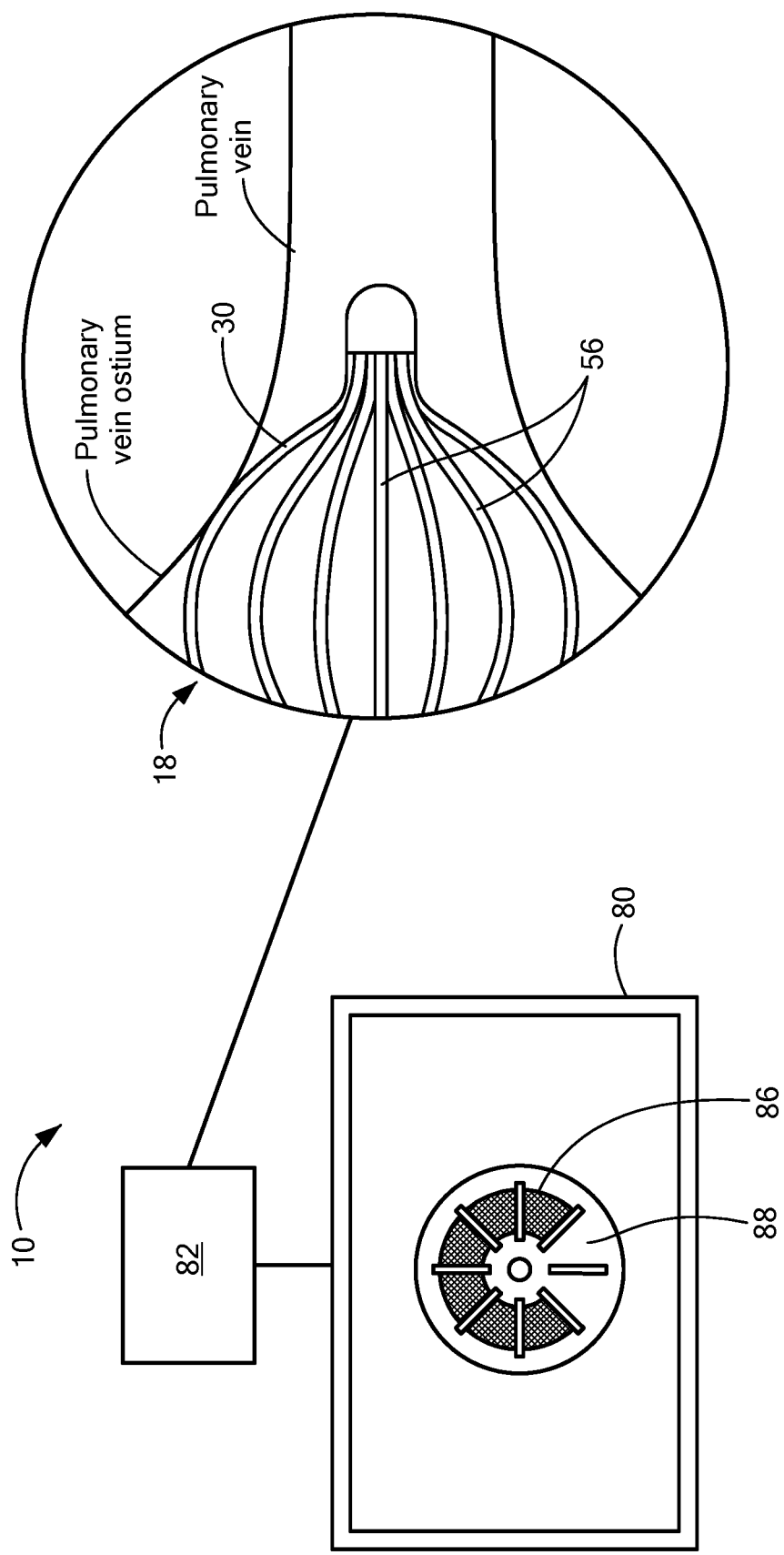
FIG. 12 shows a second simplified medical treatment system with informational display.
Figure 13:
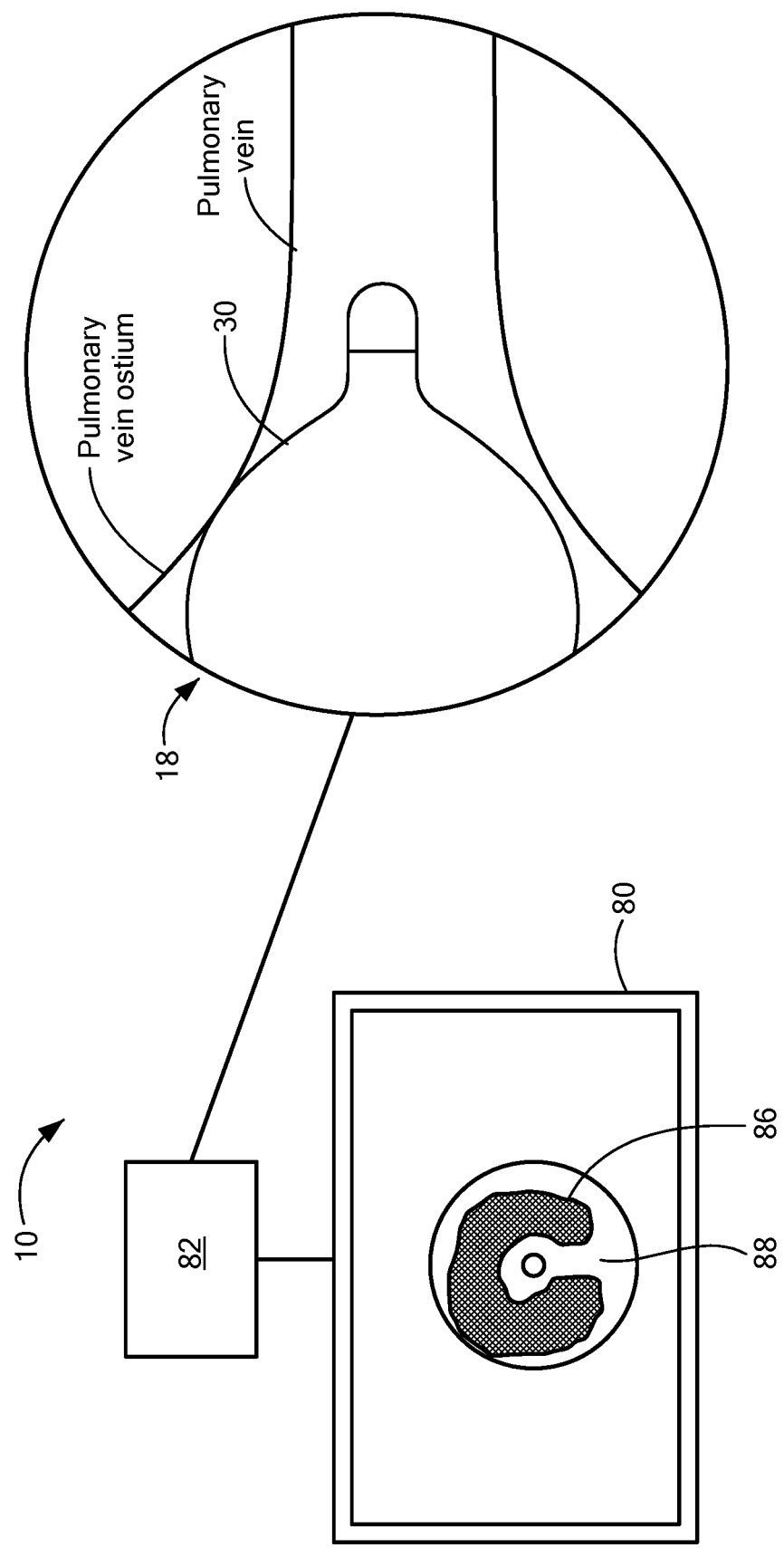
FIG. 13 shows a third simplified medical treatment system with informational display.

Referring now to FIGS. 11-13, simplified medical treatment systems with informational displays are shown to illustrate the contact sensing functionality. In all three figures, the system receives electrical signals from the contact sensing element(s) 44 in the device 12 and converts those signals to contact location information, then communicates the contact location information to the user on one or more displays 80. For example, the electrical signals may be data regarding areas of contact between the treatment element 18 and tissue. If the device 12 is used to treat a pulmonary vein ostium, for example, the display may show at least a portion of the treatment element 18 for visualization of whether contact between the cryoballoon 30 and the ostium is entirely circumferential. Thus, any gaps or areas of missing contact may quickly and easily be identified and the cryoballoon 30 can be adjusted prior to ablating or treatment the tissue. In the non-limiting example shown in FIG. 11, the location information may be displayed on an image of (for example, a stylized depiction of) the distal end of the treatment element as a generally irregularly shaped contact area, the displayed contact area 86 being determined by the contact sensing element(s) 44 registering contact with the tissue. In FIG. 11, a gap 88 or area of missing contact is shown in the bottom (or at the 6 o'clock position, as displayed) between the cryoballoon 30 and tissue. Based on this information, the user may reposition the cryoballoon 30 such that cryoballoon 30 is urged against the tissue at the gap position as well as the other positions.

The non-limiting example shown in FIG. 13 includes a contact location information display that is similar to that shown in FIG. 11, as the film 60 may detect a plurality of contact points similar to the electrode matrix of the device 12 shown in FIGS. 1-3. This information may be used similarly to that shown in FIG. 11.

In the non-limiting example shown in FIG. 12, the location information may be displayed as speedometer-type display, with the plurality of splines 56 being displayed as radially extending lines. If contact is detected by two adjacent splines 56, the display area corresponding to the cryoballoon 30 between those splines 56 is shown as part of the contact area 86. Thus, the contact area 86 is determined by the contact splines 56 registering contact with the tissue. In FIG. 12, a gap 88 or area of missing contact is shown in the bottom (or at the 6 o'clock position, as displayed) between the cryoballoon 30 and tissue. Based on this information, the user may reposition the cryoballoon 30 such that cryoballoon 30 is urged against the tissue at the gap position as well as the other positions. The system 10 may provide one or more alerts or other indications (for example, audible or visible alerts) to the user to indicate that the treatment element is in complete circumferential contact with the target tissue. Optionally, the control unit 14 may be configured to automatically initiate the delivery of cryogenic coolant to the treatment element, and thus begin the ablation procedure, when complete circumferential contact is achieved.

Although not shown, it will be understood that similar displays of information and data may be presented to the user if the treatment element 18 includes the filamentous contact sensing element(s) of FIGS. 8-10.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device for determining tissue contact, the device comprising: an elongate body including a distal portion and a proximal portion; and a treatment element coupled to the distal portion of the elongate body, the treatment element having: a first expandable element; a second expandable element, the first expandable element being within the second expandable element; a plurality of spacers spaced apart from one another and configured to maintain a distance between the first expandable element and the second expandable element; at least one contact sensing element between the first and second expandable elements, the at least one contact sensing element containing a low density material with conductive microparticles; and wherein the first expandable element has an inner surface and an outer surface, the at least one contact sensing element being on an outer surface of the first expandable element.

2. The medical device of claim 1, wherein the at least one contact sensing element is in electrical communication with a multiplexer.

3. The medical device of claim 2, wherein the device further comprises a shaft having a distal tip, the multiplexer being located at the distal tip of the shaft.

4. The medical device of claim 1, wherein the treatment element further includes an interstitial space between the first and second expandable elements, the at least one contact sensing element being in the interstitial space.

5. A medical system for determining tissue contact, the system comprising: a medical device including: an elongate body including a distal portion and a proximal portion; and a treatment element coupled to the distal portion of the elongate body, the treatment element having: a first expandable element; a second expandable element, the first expandable element being within the second expandable element; at least one contact sensing element between the first and second expandable elements, the at least one contact sensing element containing a low density material with conductive microparticles; wherein the first expandable element has an inner surface and an outer surface, the at least one contact sensing element being on an outer surface of the first expandable element; a plurality of spacers spaced apart from one another and configured to maintain a distance between the first expandable element and the second expandable element; and a control unit in communication with the medical device.

6. The medical system of claim 5, wherein the control unit includes:
   processing circuitry in communication with the at least one contact sensing element; and
   a display in communication with the processing circuitry.

7. The medical system of claim 6, wherein the at least one contact sensing element is configured to transmit electrical signals to the processing circuitry, the processing circuitry being configured to identify at last one area of the treatment element that is in contact with tissue based on the electrical signals received from the at least one contact sensing element.

8. The medical system of claim 7, wherein the processing circuitry is configured to show the identified at least one area of contact on an image of at least a portion of the treatment element.

9. The medical system of claim 7, wherein the conductive microparticles have a first conductivity when uncompressed and a second conductivity when compressed, the second conductivity being greater than the first conductivity.

10. A method for determining tissue contact, the method comprising: positioning at least a portion of a treatment element of a medical device in contact with an area of tissue, the treatment element including: a first expandable element; a second expandable element, the first expandable element being within the second expandable element, the first and second expandable elements defining an interstitial space therebetween; at least one contact sensing element in the interstitial space, the at least one contact sensing element containing a low density material with conductive microparticles; wherein the first expandable element has an inner surface and an outer surface, the at least one contact sensing element being on an outer surface of the first expandable element; and a plurality of spacers spaced apart from one another and configured to maintain a distance between the first expandable element and the second expandable element; and recording at least one electrical signal with the at least one contact sensing element and transmitting the at least one electrical signal to a control unit; identifying with the control unit at least one area of contact between the treatment element and tissue based on the at least one electrical signal; and displaying the at least one area of contact, the display including an image of at least a portion of the treatment element.

* * * * *